United States Patent [19]

Dudek

[11] 4,387,489
[45] Jun. 14, 1983

[54] CLASP FOR LOCKING A LIGATURE LOOP

[75] Inventor: Günter Dudek, Pulheim, Fed. Rep. of Germany

[73] Assignee: Prämeta Präzisionsmetaal-und Kunstofferzeugnisse G. Baumann & Co., Cologne, Fed. Rep. of Germany

[21] Appl. No.: 346,204

[22] Filed: Feb. 5, 1982

[30] Foreign Application Priority Data

Feb. 7, 1981 [DE] Fed. Rep. of Germany ....... 3104382

[51] Int. Cl.³ ...................... F16G 11/00; A44B 11/06; A61B 17/08
[52] U.S. Cl. ............................... 24/133; 24/134 KB; 24/170; 24/193; 24/248 R; 128/346
[58] Field of Search ................. 24/31 L, 69 R, 71 ST, 24/327, 328, 335, 115 R, 115 H, 115 K, 117, 24/120, 122.6, 132 WL, 133, 134 L, 248 B, 250, 24/266, 132 R, 258, 267, 248 R, 134 KB, 170, 191, 24/193; 128/346

[56] References Cited

U.S. PATENT DOCUMENTS

| 819,884 | 5/1906 | Higgins | 24/120 |
|---|---|---|---|
| 1,420,370 | 6/1922 | Ely | 24/133 |
| 1,433,829 | 10/1922 | Klaas | 24/133 |
| 1,506,335 | 8/1924 | Brown | 24/133 |
| 2,214,524 | 9/1940 | Deming | 24/250 |
| 2,227,768 | 1/1941 | Stark | 24/170 |
| 2,237,731 | 4/1941 | Freysinger | 24/250 |
| 3,290,745 | 12/1966 | Maxwell et al. | 24/120 |

Primary Examiner—Gene Mancene
Assistant Examiner—John Weiss
Attorney, Agent, or Firm—Diller, Ramik & Wight

[57] ABSTRACT

This disclosure relates to a clasp for gripping free end portions of a strap to maintain a loop thereof tightly engaged around an object, such as a portion of the human body, the clasp including upper and lower casing halves with means for releasably securing the casing halves in superposed relationship to each other to define a passage therebetween through which free end portions of a strap may pass, a clamping lever pivotally carried by the clasp to present one end portion lying at the loop end of the passage whereby to be forceably engaged by the loop when tight so that the other end of the clamping lever clamps the free end portions of the strap between it and one of the casing halves, and the lower casing half having a bridge-like cross bar lying transversely within the passage.

20 Claims, 9 Drawing Figures

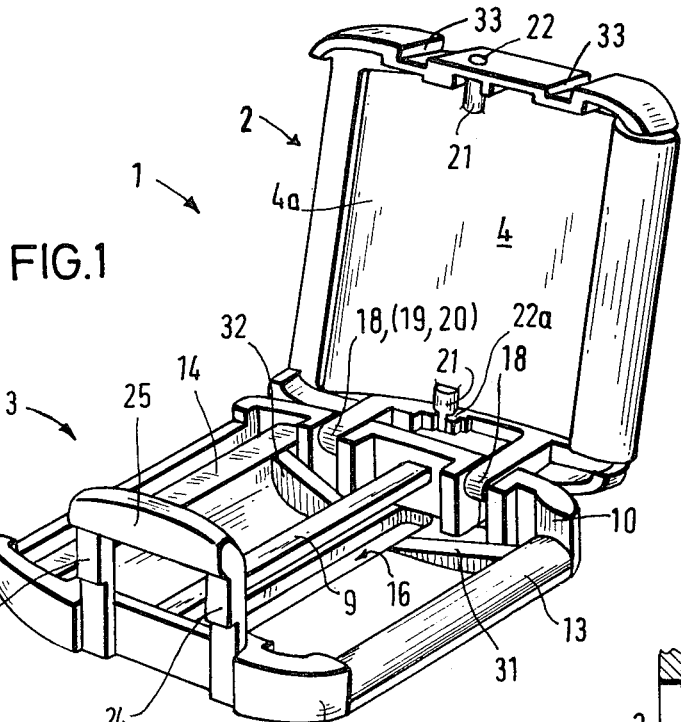
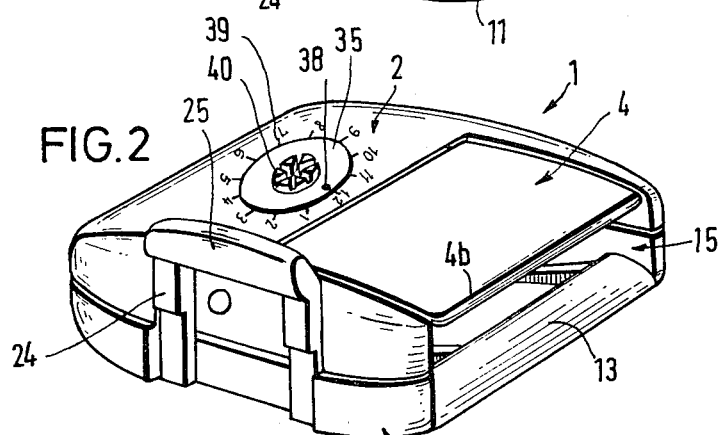
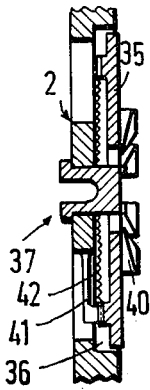
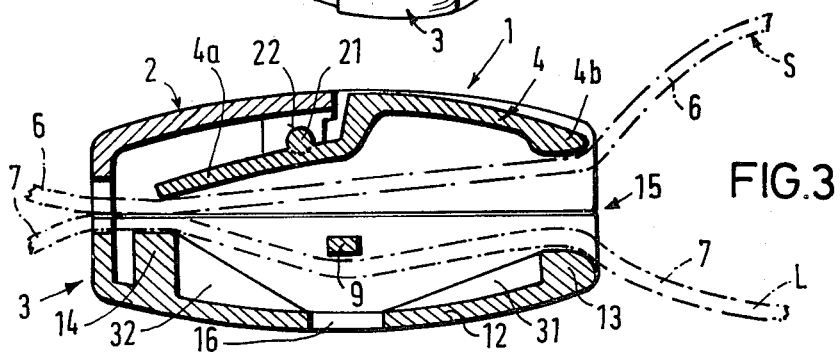

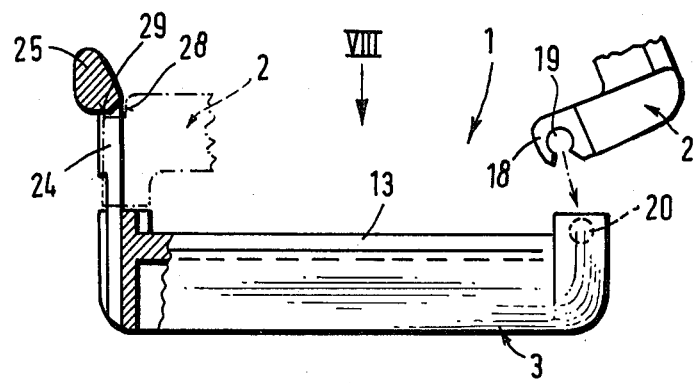
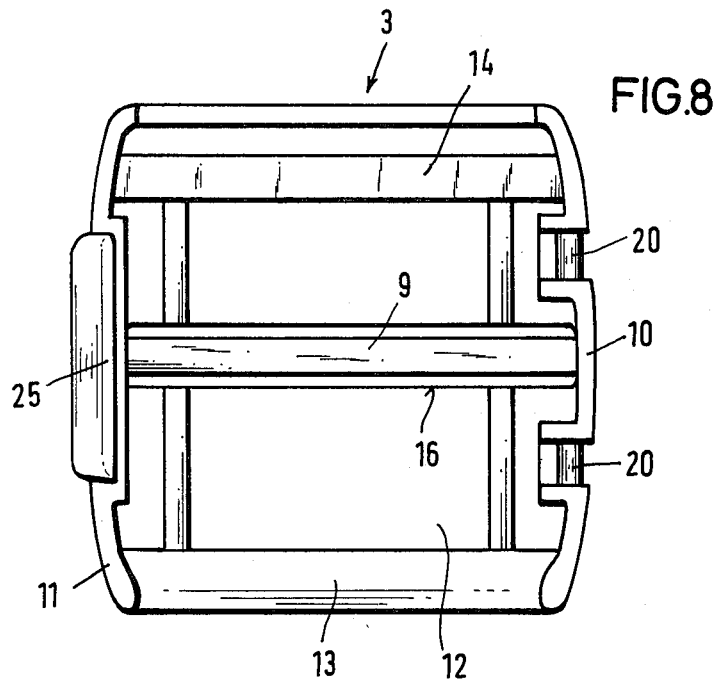

CLASP FOR LOCKING A LIGATURE LOOP

The present invention relates to a clasp for locking a ligature loop, especially to a tying-off or restricting device for bringing about restriction effects at parts of a human body in which the ends of a ligature forming a loop are passed through an elongated slot of the casing and are held fast by means of a pivoted clamping lever which may be spring-loaded.

Conventional tying-off or constricting devices for accomplishing restriction effects at different portions of a human body are relatively well known, and it is generally necessary that the end lengths of a ligature formed into a loop are inserted through a closed elongated slot in the casing of the tying-off or constricting device in order to enable the loop to be made smaller or larger by displacing the clasp relative thereto. In the case of such a clasp, the loop from the end of the lengths thereof to be tied off must be placed on the latter. In order to make possible the positioning of the ligature around and transverse to the axis of the body portion which is to be tied-off or restricted, it is moreover known to form the clasp of the tying-off device in such a way that an end length of the ligature or strap forming the loop can be unhooked from the clasp casing whereby the loop is opened directly. To this end, the clasp is provided with a screw device or a further clamping device or the like which makes possible the direct engagement or securement of one end of the ligature to and from the clasp so that the loop can be opened without it being necessary to pull one end or both ends of the ligature or strap through the closed elongated slot of the clasp casing.

A primary object of the present invention is to provide a clasp for securing in position or locking a ligature loop which makes possible the positioning of the loop around a portion of the human body which is to be restricted and the opening of the loop by a very simple manipulation through an extremely simple mechanical clasp assembly. The clasp of the invention is characterized by a clasp casing divided in the plane of its elongated slot into an upper casing half and a lower casing half with means for releasably securing the casing halves in superposed relationship to each other to define a passage therebetween through which the free end portions of a strap or ligature may pass, and the lower casing half having a bridge-like cross bar lying transversely within the passage.

By constructing the clasp so that it may be divided or opened essentially in a plane of the passage, the ends of the ligature or strap loop can be placed into the casing from above with ready access into the casing interior. After the casing halves are then closed, the ligature is by such closure also closed and locked. At the same time, the cross bar enables simple locking of one end of the ligature loop with the lower casing half so that upon opening the clasp casing, the lower casing half remains connected with the other end length of the ligature loop despite the opening of the clasp so that ony one end of the ligature loop need be manipulated to form the loop to apply the strap or ligature to a portion of the human body or remove the same end from the human body portion. Thus, though both ends of the ligature pass through the clasp, the opening of the clasp in the plane of the passage permits the ready manipulation of but a single one of the loop ends, while restraining the position of the loop end to prevent ready manipulation of the overall clasp.

In further accordance with the pressure invention, the upper casing half is mounted for lateral hinging movement upon the lower casing half, and the upper casing half carries a clamping lever to hold the two loop ends at a desired position relative to the clasp and an associated portion of the human body being constricted by the ligature or strap loop. The ability of one of the casing halves to be hinged laterally relative to the other casing half enables the casing and its ligature or strap to be manipulated very simply and provides an excellent facility for inspection, not simply of the clasp per se and its operability, but also the portion of the human body being constricted. Moreover, the hingeable nature of the casing halves relative to one another by means of the lateral hinge makes it possible for one to rapidly apply the casing and ligature loop to and remove the casing and the ligature from a portion of the human body.

Still another object of this invention is to construct the lower casing half generally of a trough-shaped configuration as viewed in longitudinal cross section. In this embodiment, ridge-shaped transverse fins are provided at front and rear edges of the trough with a cross bar being arranged therebetween and with uppermost surfaces of the front and rear edges of the trough and the cross bar lying in generally a common plane. Such a construction of the lower casing half contributes substantially towards retaining one of the loop ends within the lower casing half when the latter is threaded in an undulating fashion below the cross bar and across the upper surfaces of the front and rear edges of the trough. Though the latter permits of a slight sagging of the ligature or strap end within the lower half casing, the latter is secured against displacement along the ligature by the threaded assembly latter-noted, and the latter also precludes the lower casing half from sliding relative to the end of the ligature or strap when the casing is opened due to the frictional purchase between the strap or ligature and the upper surfaces of the front and rear fin edges and the lower surface of the cross bar. Therefore, the lower casing half is restricted in its movement relative to the ligature loop, it may yet be slid very easily from place-to-place along the length thereof when manipulated by an operator since it is merely necessary for the operator to overcome the frictional affect between the strap associated with the underside of the cross bar and the upper surfaces of the front and rear edges of the transverse trough fins.

Yet another object of this invention is to provide means for readily removing the hingeable upper casing half from the lower casing half. The upper casing half preferably includes supporting attachments in the form of generally C-shaped bearing recesses which engage in snap-like relationship over bearing journals or spindles of the lower casing half. Under normal conditions, the latter construction permits the casing halves to remain connected with one another, though hinged relative to one another. However, the possibility is also afforded of separating the hingeable casing halves completely from one another when this is ncesssary by simply unsnapping the bearing journals or spindles from the C-shaped bearing recesses.

Yet another object of this invention is to maintain the upper casing half and the lower casing half in closed condition through the snap engagement of resilient means on the lower casing half which resiliently snap into locking engagement with the upper casing half. To the latter end, the lower casing half includes an inherently resiliently attachment which has a projecting edge engageable over a ledge of the upper casing half. The natural resilience of the projecting edge of the lower casing half permits the casing halves to be closed and after closure, the inherent resilience maintains the ledge and edge in snap-locked relationship. The latter components of the snap connection are integrally formed portions of the lower casing half and the upper casing half and, thus, no additional loose components are required which, of course, are generally superfluous and can be lost.

In further accordance with this invention, a clamping lever is also preferably snap-secured to the upper casing half through trunnions integrally formed as parts of the clamping lever which snap engage in bearing blocks of the upper casing half so that separate components for connecting the clamping lever and the upper casing half are superfluous.

With the above and other objects in view that will hereinafter appear, the nature of the invention will be more clearly understood by reference to the following detailed description, the appended claims and the several views illustrated in the accompanying drawings.

IN THE DRAWINGS:

FIG. 1 is a perspective view of a novel clasp constructed in accordance with this invention, and illustrates an upper casing half and a lower casing half laterally hinged to each other with a cross bar disposed in the lower casing half transverse to a plane of a passage through the clasp or casing halves.

FIG. 2 is a perspective view of the clasp of FIG. 1, and illustrates the clasp in its closed position with a resilient projection carried by the lower casing half engaging a ledge of the upper casing half.

FIG. 3 is a longitudinal sectional view taken through the closed clasp, and illustrates a loop in phantom outline with one end portion thereof being threaded beneath the cross bar and another end portion thereof inherently urging the clamping lever in a clockwise direction to achieve a clamping effect between an end of the clamping lever remote from the loop and an underlying transverse clamping fin.

Figure 4:
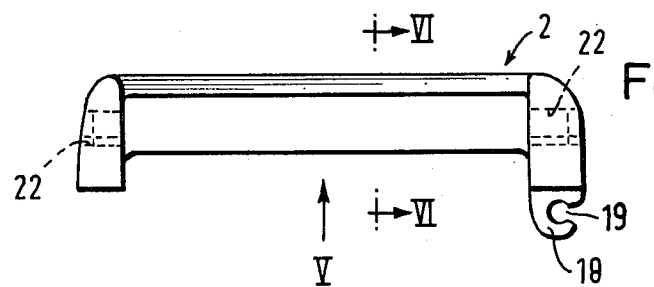

FIG. 4 is an end elevational view of the upper casing half, and illustrates one of a pair of generally C-shaped recesses for creating a lateral hinge.

Figure 5:
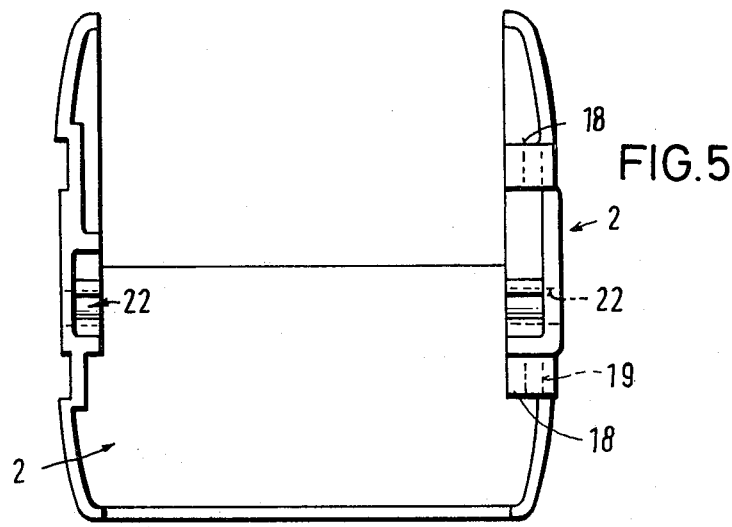

FIG. 5 is a bottom plan view of the upper casing half looking along the line V of FIG. 4, and illustrates a pair of circular recesses for receiving pins of the clamping lever.

Figure 6:
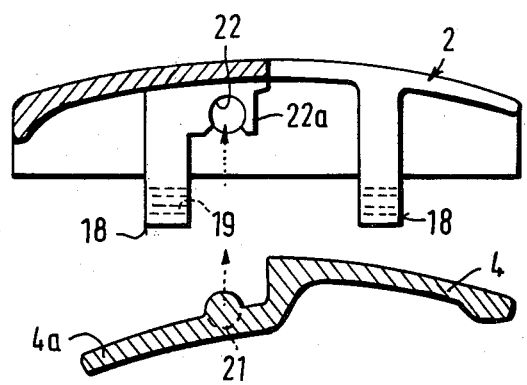

FIG. 6 is a sectional view taken generally along line VI—VI of FIG. 4, and illustrates the upper casing halves and its associated clamping lever prior to the snap connection of these components to each other.

FIG. 7 is an end elevational view, partially broken away as shown in cross section for clarity, of the lower casing half, and illustrates a portion of the upper casing half in phantom and solid outline which depicts the locking and the pivotal connection of the upper and lower casing halves.

FIG. 8 is a top plan view taken generally along line VIII of FIG. 7, and illustrates a bridge-like cross bar of the lower casing half lying transversely within a passage between a pair of opposite transverse ridges.

FIG. 9, which is located on the sheet of drawing containing FIGS. 1 through 3, is a fragmentary cross-sectional view of a time dial rotatably mounted atop the upper casing half.

A novel clasp for gripping free end portions of the strap or ligature to maintain a loop thereof tightly engaged around an object, such as an arm, leg or a like portion of the human body is generally designated by the reference numeral 1 is defined by an upper casing half 2 and a lower casing half 3 which are subdivided or disposed in substantially the median plane of the clasp 1. A clamping lever 4 is pivoted in and to the upper casing half 2 and is preferably biased by a spring (not shown) for rotation in a counterclockwise direction, as viewed in FIG. 3 of the drawings. The clamping lever 4 includes a free terminal end, end portion or lever arm 4a (FIGS. 1, 3 and 6) which bears against and, thus, clamps end portions 6, 7 of a strap S whose mid portion includes a loop L (FIG. 3). The loop L of the strap or ligature S receives an arm, leg or like portion of the human body and when the strip end portions 6, 7 are drawn to the left (FIG. 3) or the clasp 1 is moved to the right, the loop L is tightened to tie-off or restrict that portion of the human body within the loop L, as is relatively well known. This same tightening action produces forces tending to pivot the clamping lever 4 counterclockwise through the strap 6 bearing against and raising upwardly a nose 4b of the clamping lever 4. This upward force causes, of course, a downward force at the end of the lever arm 4a, thus achieving a clamping action between the lever arm 4a and one of a pair of transverse fins 14 of the clasp 1, as is most readily apparent in FIG. 3 of the drawings. A spring to augment the latter clamping force may, of course, be disposed between the lever arm 4a and the unnumbered portion of the upper casing half, as is most apparent in FIG. 3, to continually urge the lever arm 4a downwardly, as viewed in FIG. 3, or the overall clamping lever 4 in a counterclockwise direction, again as is viewed in FIG. 3 of the drawings.

The lower casing half 3 is provided in the vertical median plane with a bridge-like cross bar 9 which is an integral, one-piece, homogeneous portion of wall members, walls or sides 10, 11. The lower casing half 3 preferably is of a trough-like shape which is defined by a trough-shaped bottom or bottom wall 12 which at opposite ends terminates in ridge-shaped transverse fins or edges 13 and 14. The strip end portion or ligature end portion 7 is received in an elongated slot 15 defined between the upper casing half 2 and the lower casing half 3, and the same slot or passage 15 extends to and through the longitudinal length of the casing 1 above and below the transverse cross bar 9. The strap end portion 7 thus lies above and upon the transverse fins 13 and 14 and below and against an undersurface of the cross bar 9, and this connection effects the frictional purchase between the strap end portion 7, the ridges 13, 14 and the cross bar 9 to maintain the clasp body assembled to the lower casing half 3. Beneath the cross bar 9 and extending the length thereof is a transversely extending slot 16 formed through the trough-shaped bottom 12.

The casing halves 2 and 3 are interconnected for relative lateral hinging movement by cooperative hinge means 18, 19 and 20. The means 18 (FIGS. 4 and 6) are a pair of downwardly directed identical legs or projections which have rounded generally C-shaped bearing recesses engageable through a snap action with bearings or spindles 20 integrally formed in recesses (unnumbered) in the side wall 10 of the lower casing half 3, as is best illustrated in FIGS. 1 and 7 of the drawings. The rounded C-shaped recesses 19 simply snap over and receive the bearings 20 in a conventional fashion, and since the circular recesses 19 extend beyond 180°, this snap action comes about through the inherent resilience of the legs 18 which are preferably, along with all of the components of the clasp made from resilient material such as plastic, though metal is not excluded. The C-shaped recesses 19 preferably open outwardly of the overall clasp body, but the same may also open inwardly if desired.

The clamping lever 4 is also secured to the upper casing half 2 by a similar construction, namely, a pair of oppositely directed pivot pins or trunnions 21 of the clamping lever 4 engaged in circular recesses 22 formed in tongues 22a (FIG. 6) of the upper casing half 2. The recesses 22 extend beyond 180° and, therefore, the engagement thereof with the pins 21 is through the natural resilience of the material of the tongue 22a. Obviously, this permits the clamping lever 4 to be disengaged and remounted through a snap-action movement.

The upper casing half 2 and the lower casing half 3 are locked to each other in the closed position (FIG. 2) through integral latching means defined by inherently resilient attachments or legs 24, 24 and by a bight or handle cross bar 25 which engages a ledge 28 (FIG. 7) of the upper casing half 2. More specifically, a lowermost shoulder or edge 29 of the bight 25 overlies and engages the edge 28 of the upper casing half 2. The handle cross bar or bight 25 (FIG. 7) need but be moved left which is readily accomplished through the resilience of the legs 24 at which time the edge 29 no longer overlies the ledge 28 and the upper casing half 2 can be pivoted to its open position (FIG. 1).

The lower casing half 3 is also preferably provided at its side with the sloping surfaces 31 and 32 (FIGS. 1 and 3) which facilitate the guidance of the strap end portion 7 beneath the transverse cross bar 9. Thus, if the strap end portion 7 is inserted from right-to-left in FIG. 3, it is readily guided down the sloping surface 7 beneath and beyond the cross bar 9 and upwardly along the sloping surface 32, thus creating a slightly sagging attitude of the strap end portion 7 within the lower casing half 3, as is readily apparent in FIG. 3. The latter sloping or sagging attitude between the strap end portion 7 and the elements 13, 14 and 9 creates such a frictional purchase when the clasp is open (FIG. 1), the lower casing half 3 can not slip inadvertently relative to the strap end portion 7.

The upper casing half 2 is provided with recesses 33 into which are received the legs 24 when the casing halves 2, 3 are in their closed position (FIG. 2). Thus, the legs 24, 24 within the slots 23, 23 preclude one of the casing halves 2 from being displaced relative to the other casing half 3 in the axial or longitudinal direction of the lengths or end portions 6, 7.

When the end or nose 4b of the clamping lever 4 is pressed downwardly, as viewed in FIGS. 2 and 3, and a pull is exerted on one of the ends 6, 7 of the strap lengths to the left of the clasp 1 in FIG. 3, the clasp 1 can be bodily displaced along the lengths 6, 7 to increase or decrease the size of the ligature loop L.

As was heretofore noted, the entire clasp 1 including both halves 2, 3 thereof is preferably made of plastic material, such as polyethylene. Furthermore, all of the parts, which include but three elements, namely, the upper casing half 2, the lower casing half 3, and the clamping lever 4, are held to each other by easily assembled and disassambled snap connectors and, thus, further components have become totally unnecessary and superfluous. This results in a straightforward construction with the various parts being easily disengaged, disassembled, re-engaged and reassembled. The clasp 1 is universally suitable for the most varied purposes when the ligature loop L has to be tightened, and this may take place particularly for the tying-off or constricting parts of the body to achieve restriction effects. Therefore, though designed particularly for medical types of utilization, the overall clasp 1 may also be utilized where articles are merely held together by means of a loop L, such as documents, impedement and the like.

Although only a preferred embodiment of the invention has been specifically illustrated and described herein, it is to be understood that minor variations may be made in the apparatus without departing from the spirit and scope of the invention, as defined in the appended claims.

What is claimed is:

1. A clasp for gripping free end portions of a strap to maintain a loop thereof tightly engaged around an object such as a portion of the human body, said clasp comprising an upper casing half and a lower casing half and means for releasably securing said casing halves in superposed relation to each other to define a passage therebetween through which the free end portions of a strap may pass thereby forming a loop end at one end portion of a clamping lever, said clamping lever being pivotally carried by said clasp to present said one end portion lying at the loop end of said passage whereby to be forcibly engaged by the loop when tight so that the other end of said clamping lever clamps the free end portions of the strap between it and one of the casing halves, said lower casing half having a bridgelike cross bar lying transversely within said passage.

2. A clasp as defined in claim 1 wherein said means for releasably securing the casing halves in superposed relation includes hinge means pivotally connecting said halves about an axis parallel to but to one side of said passage.

3. A clasp as defined in claim 1 or 2 wherein said clamping lever is pivotally carried by the upper casing half.

4. A clasp as defined in claim 3 wherein said lower casing half is provided with an upstanding and transversely extending rib at said loop end of the passage and with an upstanding and transversely extending second rib at the other end of said passage, the underside of said cross bar lying below the level of said ribs whereby one of said free ends constrained to undulate below said cross bar.

5. A clasp as defined in claim 1 or 2 wherein said lower casing half is provided with an upstanding and trtansversely extending rib at said loop end of the passage and with an upstanding and transversely extending second rib at the other end of said passage, the underside of said cross bar lying below the lever of said ribs whereby one of said free ends is constrained to undulate below said cross bar.

6. A clasp as defined in claim 2 wherein said hinge means comprises bearing journals on said lower casing half and C-shaped bearing recesses in said upper casing half receiving said bearing journals.

7. A clasp as defined in claim 3 wherein said hinge means comprises bearing journals on said lower casing half and C-shaped bearing recesses in said upper casing half receiving said bearing journals in forcibly snap-fitted relation.

8. A clasp as defined in claim 4 wherein said hinge means comprises bearing journals on said lower casing half and C-shaped bearing recesses in said upper casing half receiving said bearing journals in forcibly snap-fitted relation.

9. A clasp as defined in claim 5 wherein said hinge means comprises bearing journals on said lower casing half and C-shaped bearing recesses in said upper casing half receiving said bearing journals in forcibly snap-fitted relation.

10. A clasp as defined in claim 1 or 2 wherein said means for releasably securing said casing halves in superposed relation includes resilient means.

11. A clasp as defined in claim 3 wherein said means for releasably securing said casing halves in superposed relation includes resilient means on said lower casing half adapted to resiliently snap into locking engagement with the upper casing half.

12. A clasp as defined in claim 4 wherein said means for releasably securing said casing halves in superposed relation includes resilient means on said lower casing half adapted to resiliently snap into locking engagement with the upper casing half.

13. A clasp as defined in claim 5 wherein said means for releasably securing said casing halves in superposed relation includes resilient means on said lower casing half adapted to resiliently snap into locking engagement with the upper casing half.

14. A clasp as defined in claim 6 wherein said means for releasably securing said casing halves in superposed relation includes resilient means on said lower casing half adapted to resiliently snap into locking engagement with the upper casing half.

15. A clasp according to claim 1 or 2 characterised in that a transversely-extending recess is arranged in the bottom of the lower casing half below the cross bar.

16. A clasp according to claim 1 or 2 characterised in that the clamping lever includes trunnions snap-fitted into a generally C-shaped recesses in the upper casing half.

17. A clasp according to claim 3 characterised in that the clamping lever includes trunnions snap-fitted into a generally C-shaped recesses in the upper casing half.

18. A clasp according to claim 4 characterised in that the clamping lever includes trunnions snap-fitted into a generally C-shaped recesses in the upper casing half.

19. A clasp according to claim 5 characterised in that the clamping lever includes trunnions snap-fitted into a generally C-shaped recesses in the upper casing half.

20. A clasp according to claim 6 characterised in that the clamping lever includes trunnions snap-fitted into a generally C-shaped recesses in the upper casing half.

* * * * *